United States Patent
Dahmane et al.

(10) Patent No.: US 8,759,367 B2
(45) Date of Patent: Jun. 24, 2014

(54) COMPOUNDS AND METHODS FOR THE PREVENTION AND TREATMENT OF CANCER

(75) Inventors: Nadia Dahmane, Philadelphia, PA (US); Jeffrey D. Winkler, Wynnewood, PA (US); Andre Isaacs, Worcester, MA (US)

(73) Assignees: The Wistar Institute, Philadelphia, PA (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/880,223

(22) PCT Filed: Oct. 4, 2011

(86) PCT No.: PCT/US2011/054698
§ 371 (c)(1),
(2), (4) Date: Apr. 18, 2013

(87) PCT Pub. No.: WO2012/054228
PCT Pub. Date: Apr. 26, 2012

(65) Prior Publication Data
US 2013/0203794 A1    Aug. 8, 2013

Related U.S. Application Data

(60) Provisional application No. 61/394,984, filed on Oct. 20, 2010.

(51) Int. Cl.
*C07D 471/10*    (2006.01)

(52) U.S. Cl.
USPC .............................. 514/278; 435/375; 546/15

(58) Field of Classification Search
None
See application file for complete search history.

(56) References Cited

FOREIGN PATENT DOCUMENTS

WO    WO 2009/058945 A1    5/2009

OTHER PUBLICATIONS

Chen et al. "Inhibition of Hedgehog Signaling by Direct Binding of Cyclopamine to Smoothened" Genes & Development 2002 16:2743-2748.
Hall et al. "A Potential Catalytic Site Revealed by the 1.7-Å Crystal Structure of the Amino-terminal Signalling Domain of Sonic Hedgehog" Nature 1995 378:212-216.
Liu et al. "Hedgehog Signaling and Bmi-1 Regulate Self-renewal of Normal and Malignant Human Mammary Stem Cells" Cancer Research 2006 66(12):6063-6071.
Sanchez, P. and Altaba, A. R. "In vivo Inhibition of Endogenous Brain Tumors Through Systemic Interference of Hedgehog Signaling in Mice" Mechanisms of Development 2005 122:223-230.
International Search Report from PCT/US11/54698, Mar. 13, 2012, PCT.
International Preliminary Report on Patentability from PCT/US11/54698, May 2, 2013, PCT.

*Primary Examiner* — Janet L Andres
*Assistant Examiner* — Timothy R Rozof
(74) *Attorney, Agent, or Firm* — Licata & Tyrrell P.C.

(57) ABSTRACT

The present invention relates to compounds for modulating sonic hedgehog signaling and preventing or treating cancer.

10 Claims, 1 Drawing Sheet

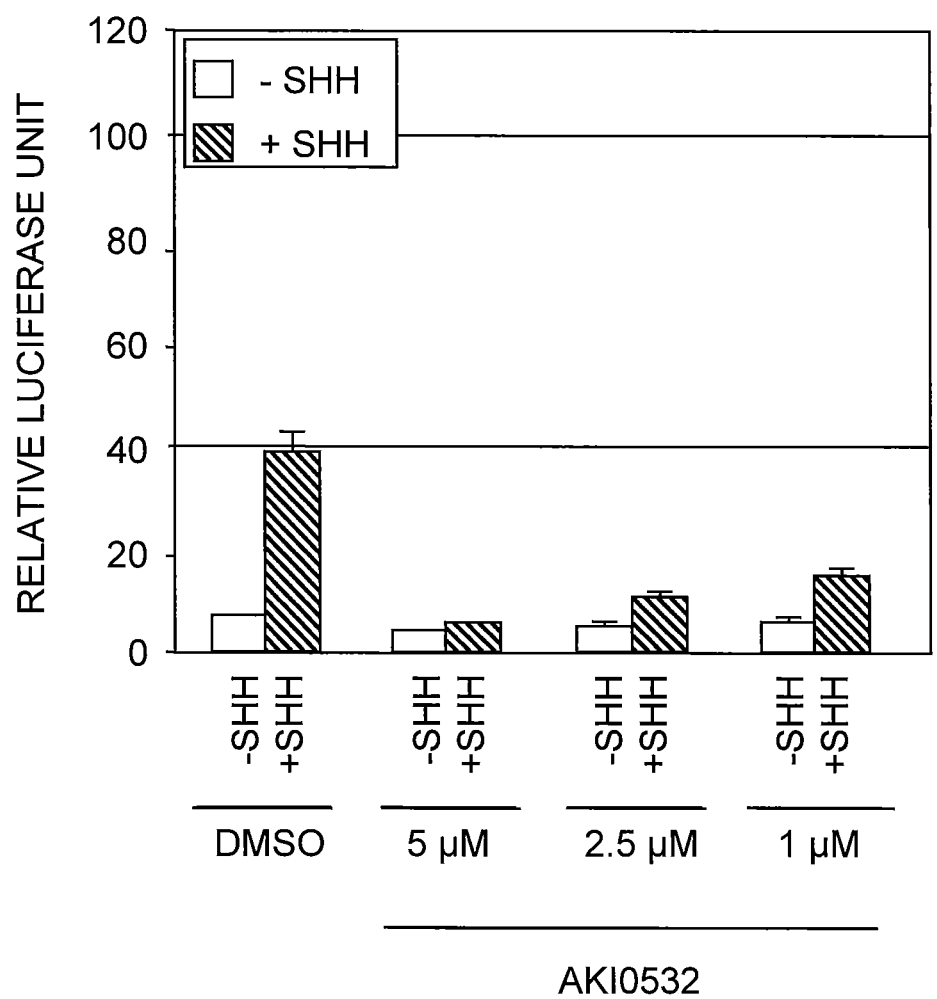

ical Stage Application of PCT/US2011/054698 filed Oct. 4, 2011 and claims the benefit of priority from U.S. Provisional Application Ser. No. 61/394,984 filed Oct. 20, 2010, the contents of each of which are incorporated herein by reference in their entirety.

This invention was made with government support under contract number CA 134983 awarded by the National Institutes of Health. The government has certain rights in the invention.

INTRODUCTION

Background of the Invention

Breast cancer is the most common cancer among women, other than skin cancer. It is the second leading cause of cancer death in women, after lung cancer. Almost 180,000 women in the United States will be diagnosed with invasive breast cancer in 2007 and over 40,000 women will die from the disease in a year. It has been suggested that the failure of existing therapies may be due to the presence of a subpopulation of cells in the bulk of the tumor that are resistant to radiotherapy and chemotherapy. These cells, called breast cancer stem cells, have self-renewal and multi-pluripotency characteristics. Sonic hedgehog (SHH) signaling plays an important role during normal mammary gland development and it has been recently demonstrated that this signaling pathway is activated in breast carcinoma and that it regulates the behavior of breast cancer stem cells. The SHH pathway therefore constitutes a therapeutic target for the development of new breast cancer therapeutics.

The SHH gene belongs to a human gene family with three genes that encode secreted glycoproteins implicated in multiple developmental processes, including the regulation of cell identity, proliferation and survival (Ingham & McMahon (2001) Genes Dev. 15:3059-3087). SHH is the most widely expressed of the family and the one that has been implicated in human cancer. SHH signals are conveyed intracellularly by the membrane proteins PATCHED (PTCH1) and SMOOTHENED (SMOH). In the absence of SHH, PTCH11 inhibits SMOH, thereby inhibiting the downstream transduction cascade. On binding of SHH to PTCH1, inhibition is released, SMOH signals, and a macromolecular complex that is associated with the cytoskeleton is activated. The reception of the SHH signal in the responding cell results in the activation of target genes through the transcription factors of the GLI family. Three GLI genes have been identified that code for proteins with partially divergent functions (Ruiz i Altaba, et al (2003) Curr. Opin. Genet. Dev. 13:513-521). In general, GLI1 acts primarily as an activator, GLI2 as both an activator and repressor, and GLI3 mostly as a repressor (Ruiz i Altaba, et al. (2003) Curr. Opin. Genet. Dev. 13:513-521; Jacob & Briscoe (2003) EMBO Rep. 4:761-765). However, these functions are context-dependent (Bai, et al. (2004) Dev. Cell. 6:103-115; Karlstrom, et al. (2003) Development 130:1549-1564; Persson, et al. (2002) Genes Dev. 16:2865-2878; Ruiz i Altaba (1998) Development 125:2203-2212). SHH-GLI pathway signaling has been shown to be blocked by interaction of a plant-derived alkaloid known as cylopamine with SMOH (Chen, et al. (2002) Genes Dev. 16:2743-2748).

The first link of SHH to cancer was the identification of mutations in the PTCH1 gene in patients with Gorlin's or Basal Cell Nevus Syndrome (Hahn, et al. (1996) Cell 85:841-851; Johnson, et al. (1996) Science 272:1668-1671). These patients develop a variety of tumors at higher frequency and with an earlier onset that normal, including basal cell carcinoma (BCC) of the skin and medulloblastoma of the cerebellum. It has also been shown that SHH signaling is active in the majority of sporadic BCCs (Dahmane, et al. (1997) Nature 389:876-881) and in brain tumors, including medulloblastomas and gliomas (Dahmane, et al. (2001) Development 128: 5201-5212; Berman, et al. (2002) Science 297:1559-1561; Clement, et al. (2007) Curr. Biol. 17:165-172). The SHH signaling pathway has also been linked to prostate cancer (Karhadkar, et al. (2004) Nature 431:707-712; Sanchez, et al. (2004) Proc. Natl. Acad. Sci. USA 101:12561-12566; Sheng, et al. (2004) Mol. Cancer. 3:29), small cell lung cancer (Watkins, et al. (2003) Nature 422:313-317), lung adenocarcinoma (Yuan, et al. (2007) Oncogene 26:1046-1055), melanoma (Stecca, et al. (2007) Proc. Natl. Acad. Sci. USA 104: 5895-5900), and pancreatic cancer (Berman, et al. (2003) Nature 425:846-851). Importantly, treatment of cancer cells derived form these various types of cancer with cyclopamine in vitro or in vivo induces a decrease in proliferation, an increase of apoptosis, or a decrease of metastasis. The effects of cyclopamine are specific as they are rescued by expression of GLI1, which acts downstream of SMOH in the signaling pathway; further, the effects of cyclopamine are mimicked by inhibition of SMOH by RNA interference (Clement, et al. (2007) Curr. Biol. 17:165-172; Stecca, et al. (2007) Proc. Natl. Acad. Sci. USA 104:5895-5900).

Studies have also linked the SHH signaling pathway with mammary gland function and breast cell proliferation. Studies in transgenic mice, specifically Gli2$^{+/-}$ and Ptc1$^{+/-}$, have demonstrated a role for SHH signaling in mammary gland development (Lewis, et al. (2001) Dev. Biol. 238:133-144; Lewis, et al. (1999) Development 126:5181-5193), although the precise role of the SHH signaling pathway in this process remains to be elucidated. Moreover, constitutive activation of the SHH pathway in transgenic mice through the expression of activated SMOH in the mammary epithelium results in increased proliferation of progenitors cells and leads to ductal dysplasia (Moraes, et al. (2007) Development 134:1231-1242). In humans, mammary stem cells have active SHH signaling and treatment of mammosphere cultures, generated from mammary stem cells, with recombinant SHH induces an increase in the number of sphere-initiating cells and mammosphere size (Liu, et al. (2006) Cancer Res. 66:6063-6071). Addition of cyclopamine to mammospheres has the inverse effect (Liu, et al. (2006) Cancer Res. 66:6063-6071). Malignant mammospheres obtained from human breast cancer samples respond in a similar manner to modulation of SHH signaling (Liu, et al. (2006) supra). Thus, as in the case of gliomas (Clement, et al. (2007) Curr. Opin. Biol. 17:165-172), stem cells in breast cancers appear to require an active SHH pathway for continued proliferation and survival.

While cyclopamine is effective in inhibiting hedgehog signaling, synthesis of this molecule can be challenging. Therefore, there is a need for new therapeutics for treatment of cancer, including breast cancer, and the SHH pathway is an attractive target.

SUMMARY OF THE INVENTION

The present invention is a compound having the structure:

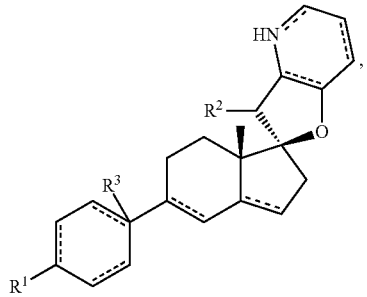

wherein the dashed bonds are present or absent; $R^1$ and $R^2$ are each independently selected from the group of H, —OH, =O, a halo group, a phenyl group, or a $C_{1-6}$ alkyl group; and $R^3$ is H, —OH, or a $C_{1-6}$ alkyl group. In one embodiment, the compound is AKI0532 or a compound set forth in Table 1. In another embodiment, the compound is used in the manufacture of a medicament for the prevention or treatment of cancer. Accordingly, a pharmaceutical composition a compound of the invention in admixture with a pharmaceutically acceptable carrier is also provided, wherein said composition is formulated for parenteral, transdermal, oral, subcutaneous, intrapulmonary, topical or intranasal administration.

A method for inhibiting sonic hedgehog signaling by contacting a cell, e.g., a cancer cell, with a compound of the invention is also provided, wherein said method can be carried out in vitro.

Moreover, the invention also features a method for preventing or treating cancer by administering to a subject in need of treatment an effective amount of a pharmaceutical composition containing a compound of the invention. In one embodiment, the cancer is breast cancer, prostate cancer, small cell lung cancer, lung adenocarcinoma, melanoma, pancreatic cancer, basal cell carcinoma, medulloblastoma, or meningioma. In another embodiment, the cancer has metastasized.

BRIEF DESCRIPTION OF THE DRAWINGS

FIG. 1 shows that AKI0532 inhibits GLI1-driven reporter activity mediated by exogenous SHH. Shh-light2 cells (3T3 clone stably transfected with a GLI-dependent firefly luciferase plasmid) were treated with carrier DMSO as control or AKI0532 (5, 2.5, or 1 µM in DMSO) either alone (−SHH) or in combination with SHH (+SHH) for 2 days.

DETAILED DESCRIPTION OF THE INVENTION

A novel antagonist of Sonic Hedgehog function, designated herein as AKI0532, has now been synthesized. This compound shares structural similarities with cyclopamine and, like cyclopamine, inhibits GLI1-driven reporter activity mediated by exogenous SHH (Sonic Hedgehog protein)(FIG. 1). Accordingly, the present invention provides AKI0532, which has the following structure.

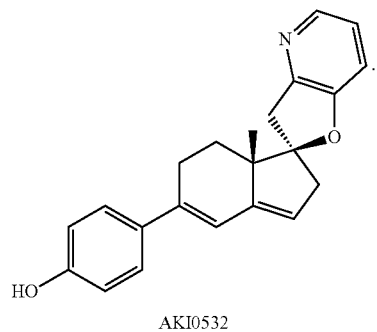

AKI0532

In addition, AKI0532 can be used as a lead compound to generate additional, structurally related compounds or derivatives that inhibit SHH signaling. For example, the instant compound can be modified to include additional substituents (e.g., O, N, S, OH, $CH_3$, halo groups; phenyl groups, alkyl groups, etc.), remove substituents (e.g., O, N, S, OH, $CH_3$, halo groups, phenyl groups, alkyl groups, etc.), or substitute groups (e.g., substitute one halo group for another) in order to provide compounds with improved activity and/or efficacy. In this respect, it is contemplated that compounds containing substituents similar to those of cyclopamine analogs known in the art will modulate the SHH signaling pathway. Examples of cyclopamine analogs and substituents of the same are described in WO/2009/058945. In particular embodiments, examples of analogs of AKI0523 are set forth in Table 1.

TABLE 1

Analog

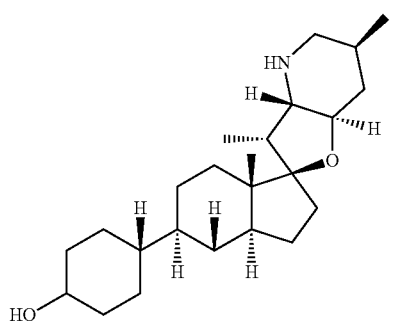

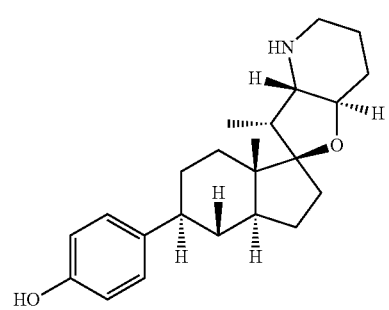

TABLE 1-continued

Analog

In this respect, particular embodiments of the invention feature a compound having the formula:

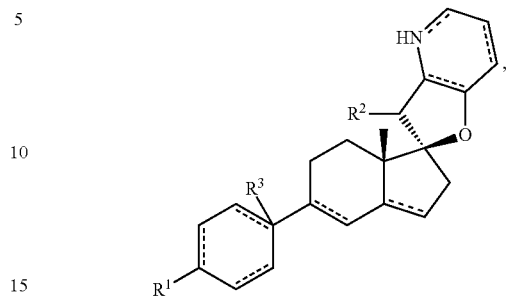

wherein the dashed bonds are present or absent; $R^1$ and $R^2$ are each independently selected from the group of H, —OH, =O, a halo group, a phenyl group, or a $C_{1-6}$ alkyl group; and $R^3$ is H, —OH, or a $C_{1-6}$ alkyl group.

To demonstrate SHH agonistic or antagonistic activity, AKI0523 derivatives or analogs can be screened via in silico, in vitro, or in vivo methods. For example, AKI0532 analogs shown in Table 1 can be subjected to a battery of tests that are commonly used to assess effects on SHH activity and to determine specificity. As exemplified herein for AKI0532, one screen involves examining the activation of the SHH pathway using the well-established cell line, SHH-Light2 cells. This cell line is a 3T3 clone that stably expresses a GLI-dependant firefly luciferase (Taipale, et al. (2000) *Nature* 406:1005-1009). Treatment of these cells with recombinant SHH activates GLI-dependant firefly luciferase and this SHH-induced activation has been shown to be inhibited when cells are also treated with cyclopamine (Taipale, et al. (2000) supra). Concentrations of each compound, ranging from 20 µM to 1 µM, can be tested. SHH-Light2 cells are seeded 24 hours prior to treatment. They were then cultured for an additional 48 hours in standard serum-containing media prior to analysis. GLI-binding site luciferase activities are measured using a commercially available luciferase reporter assay system. Treatment of SHH-Light2 cells with recombinant SHH (200 ng) results in strong induction of reporter activity. $IC_{50}$ values are determined and are compared to that of AKI0532 in the same assay in order to assess which of the AKI0532 analogs have the highest levels of SHH inhibitory activity.

It has previously been shown that SHH is a potent mitogen for granule neuron precursors (GNPs) purified from postnatal mouse cerebella (Dahmane & Ruiz I Altaba (1999) *Development* 126:3089-3200). This well-established system can be used to test AKI0532 and analogs thereof for their activity in inhibiting this proliferative response of GNPs to SHH.

In addition, a series of additional tests can be used to further characterize the biological activity of AKI0532, and AKI0532 derivatives and analogs. For example, to examine the specificity of activity, rescue experiments are performed in cells expressing GLI1. Specificity is shown when effects are rescued by GLI1, whereas any non-specific effects are not reversed by GLI1.

Moreover, the blockade of SHH-induction of alkaline phosphatase activity in mouse cells can be determined. Treatment of mouse C3H10T1/2 cells with SHH (or transfection with GLI1 or GLI2, which can mediate SHH signals), leads to their osteogenic differentiation and the expression of alkaline phosphatase (Roessler, et al. (2003) *Proc. Natl. Acad. Sci. USA* 100:13424-13429; Ruiz I Altaba (1999) *Development*

126:3205-3216). Therefore, it can be determined whether SHH-mediated alkaline phosphatase expression can be blocked upon treatment with AKI0532 or AKI0532 derivatives or analogs.

Biological activity of AKI0532, and AKI0532 derivatives and analogs of the invention can also be analyzed in breast cancer cells to demonstrate therapeutic efficacy. Previous studies have shown that breast cancer stem cells respond to cyclopamine. Therefore, cancer mammospheres, prepared form human breast cancer samples, are cultured (Liu, et al. (2006) *Cancer Res.* 66:6063-6071) and exposed to AKI0532 or AKI0532 derivatives or analogs of the present invention. Medical history, cancer type, stage and other parameters of the breast cancer samples are then correlated with the inhibitory activity of the AKI0532 or AKI0532 derivatives or analogs.

Conventional breast cancer cell lines can also be employed to demonstrate the efficacy of AKI0532 or AKI0532 derivatives or analogs of the invention. For example, activity of SHH pathway can be assessed by monitoring the expression of GLI1 in the presence and absence of a compound of interest. Cell lines of use in this analysis include the MCF7 and T47D cell lines.

In addition to growth in situ, metastasis is a major problem in breast cancer. It has been shown that systemic cyclopamine treatment in mice injected with metastatic melanoma cells blocks metastatic growth (Stecca, et al. (2007) *Proc. Natl. Acad. Sci. USA* 104:5895-5900). Therefore, AKI0532 or AKI0532 derivatives or analogs of the present invention can be analyzed for anti-metastatic potency as well as anti-proliferative and pro-apoptotic activities. Experiments are performed to test for AKI0532-, AKI0532 derivative- or AKI0532 analog-mediated inhibition of common breast cancer metastases (e.g., lung, liver, brain) after tail vein injection of metastatic breast cancer cells in mice. Breast cancer cell lines whose metastatic properties (4T1) have been characterized, and that stably express Luciferase are employed to visualize in vivo the metastatic cells. Metastases development is examined 1-2 weeks following injection by injecting D-luciferin to anesthesized mice and image analysis.

Another screening assay involves in vivo treatment of chick embryos. Treatment of developing chick embryos (HH stage 10) with cyclopamine has been shown to lead to a cyclopic phenotype typical of loss of SHH signalling (Cooper, et al. (1998) *Science* 280:1603-1607). This assay can also provide a measure of the potential toxicity of compounds of the present invention.

AKI0532, and analogs and derivatives thereof, of the invention can also be tested using a tumor mouse model that has been shown to react to either cyclopamine (Sanchez & Ruiz I Altaba (2005) *Mech. Dev.* 122:223-230) or a small drug targeting the SHH pathway (Romer, et al. (2004) *Cancer Cell* 6:229-240). Ptc1$^{+/-}$ p53$^{-/-}$ mice develop medulloblastoma within a month after birth and die at 2 months on average. These mice represent a relevant model to test for effectiveness of the compounds of the present invention to treat tumors in vivo. Mice are administered one or more compounds orally in their diet or are injected intraperitoneally, and brain tumor development is assayed both with behavioural methods (circling, abnormal gait, etc) and by histological examination.

Furthermore, the compounds of the present invention can be tested in a nude mouse model with human breast cancer xenografts. Compounds are tested on orthotopical grafts of human breast cancer cell lines and primary tumors. These experiments involve grafting human tumor cells to the mouse breast fat pads using, e.g., the "humanized" mouse mammary fat pad protocol which reflects human breast cancer (Kuperwasser, et al. (2004) *Proc. Natl. Acad. Sci. USA* 101:4966-4971; Proia & Kuperwasser (2006) *Nat. Protocol* 206-214). After the tumor has developed and attained a reasonable size, compounds of interest are injected intra- and peri-tumorally or intraperitoneally and tumor size is measured daily with a calliper.

AKI0532, as well as analogs and derivatives thereof, find application in inhibiting sonic hedgehog signaling and in the prevention and treatment of various cancers, including breast cancer, or for use in prevention and treatment of any disease shown to be linked to SHH signaling pathways. Accordingly, the present invention features in vitro and in vivo methods for using said AKI0532, and AKI0532 analogs or derivatives, to inhibit sonic hedgehog signaling. Thus, in accordance with one embodiment, a cell (e.g., a cancer cell) is contacted with AKI0532, or an AKI0532 analog or derivative, in vitro and sonic hedgehog signaling in the cell is inhibited. In accordance with another embodiment, an effective amount of AKI0532, or an AKI0532 analog or derivative, is used in the preparation of a medicament for the prevention or treatment of a disease or condition mediated by sonic hedgehog signaling. When such a medicament is administered to a subject in need of treatment, e.g., a subject having or at risk of having a disease or condition mediated by sonic hedgehog signaling, the sonic hedgehog signaling pathway is inhibited and the disease or condition is prevented or treated. Various diseases or conditions mediated by sonic hedgehog signaling cell are well-known to those skilled in the art. Such disease and conditions are generally characterized as proliferative disorders such as breast cancer, prostate cancer, small cell lung cancer, lung adenocarcinoma, melanoma, pancreatic cancer, basal cell carcinoma (BCC), medulloblastoma, and meningiomas. Moreover, inhibition of the sonic hedgehog signaling pathway, as described herein, may be useful in inhibiting cancer metastasis.

AKI0532, or an AKI0532 analog or derivative, may be particular useful in the prevention or treatment of medullablastoma. Medulloblastoma is a malignancy of the cerebellum with the highest incidence of all pediatric brain tumors and existing therapies are not optimal. Medulloblastomas are thought to recapitulate developmental events but in a deregulated fashion. It has been shown that the Sonic Hedgehog (SHH) signaling pathway is critical for the development of the cerebellum where its deregulation can lead to medulloblastoma. This pathway is transduced in cells responding to the secreted factor SHH by the activation of zinc finger transcription factors of the GLI family. A tight regulation of this signaling pathway is thus critical not only for normal brain development but also during adulthood for homeostasis and for the prevention of tumor formation. In the developing cerebellum, SHH regulates the proliferation of granule cell precursors (GCPs) which are thought to be the cells at the origin of medulloblastomas.

Most medulloblastomas are sporadic, but they also occur in familial syndromes. Mutations in PATCHED1 (PTCH1), a negative regulator of SHH signaling, are associated with Gorlin's syndrome and also occur in sporadic medulloblastoma. Mice heterozygous for mutations in Ptc1 also develop medulloblastomas showing a higher penetrance on a p53 background. Mutations activating the SHH pathway may be found in approximately 10-25% of all sporadic medulloblastomas. However, alterations in this pathway through epigenetic events may greatly elevate this number. One possibility is that most human sporadic medulloblastomas may require sustained SHH signaling. Pharmacological inhibition of the SHH pathway in Ptch1$^{+/-}$; p53$^{-/-}$ mice inhibits medulloblastoma growth, indicating the utility of the instant analogs in preventing or treating medullablastoma.

AKI0532, or an AKI0532 analog or derivative, can be administered by any suitable means, including parenteral, subcutaneous, intrapulmonary, and intranasal administration. Parenteral infusions include intramuscular, intravenous, intraarterial, or intraperitoneal administration. AKI0532, or an AKI0532 analog or derivative, can also be administered by inhalation. AKI0532, or an AKI0532 analog or derivative, may also be administered transdermally in the form of a slow-release cutaneous or subcutaneous implant for example, or orally in the form of capsules, powders or granules. Compounds of the present invention can also be applied locally directly on the epidermis (e.g., topically), in the form of a cream or ointment, for example, in the case of BCC.

Generally, when used in the prevention or treatment of a disease or condition, AKI0532, or an AKI0532 analog or derivative, is in admixture with a pharmaceutically acceptable carrier and at an appropriate dose. Such pharmaceutical compositions can be prepared by methods and contain carriers which are well-known in the art. A generally recognized compendium of such methods and ingredients is Remington: The Science and Practice of Pharmacy, 21st ed. Lippincott Williams & Wilkins: Philadelphia, Pa., 2005. A pharmaceutically-acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the subject being treated.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The invention provides any pharmaceutical preparations and compositions containing one or more of the compounds of the invention for use in the method of the invention. The form will vary depending upon the route of administration. For example, compositions for injection can be provided in the form of an ampule, each containing a unit dose amount, or in the form of a container containing multiple doses.

Compounds of the invention can be formulated into the pharmaceutical composition as neutralized pharmaceutically acceptable salt forms. These include the acid addition salts which are formed with inorganic acids such as, for example, hydrochloric or phosphoric acid, or organic acids such as acetic, oxalic, tartaric and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery of the instant compounds may be achieved by selecting appropriate macromolecules, for example, polyesters, polyamino acids, polyvinyl pyrrolidone, ethylenevinylacetate, methylcellulose, carboxymethylcellulose, protamine sulfate, or lactide/glycolide copolymers. The rate of release of the compounds of the invention may be controlled by altering the concentration of the macromolecule.

Another method for controlling the duration of action includes incorporating AKI0532, or an AKI0532 analog or derivative, into particles of a polymeric substance such as polyesters, polyamino acids, hydrogels, polylactide/glycolide copolymers, or ethylenevinylacetate copolymers. Alternatively, it is possible to entrap compounds in microcapsules prepared, for example, by coacervation techniques or by interfacial polymerization, for example, by the use of hydroxymethylcellulose or gelatin-microcapsules or poly(methylmethacrolate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

The selected dosage level will depend upon a variety of factors including the activity of the particular compound of the present invention employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of a compound at levels lower than that required in order to achieve the desired therapeutic effect and gradually increase the dosage until the desired effect is achieved. This is considered to be within the skill of the artisan and one can review the existing literature on a specific compound or similar compounds to determine optimal dosing.

The invention is described in greater detail by the following non-limiting examples.

EXAMPLE 1

Synthesis of AKI0532

The synthesis of AKI0532 from the commercially available (S)-(+)-2,3,7,7a-Tetrahydro-7a-methyl-1H-indene-1,5 (6H)-dione (Aldrich) is depicted in Scheme 1.

SCHEME 1

Scheme

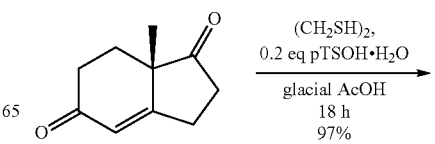

-continued
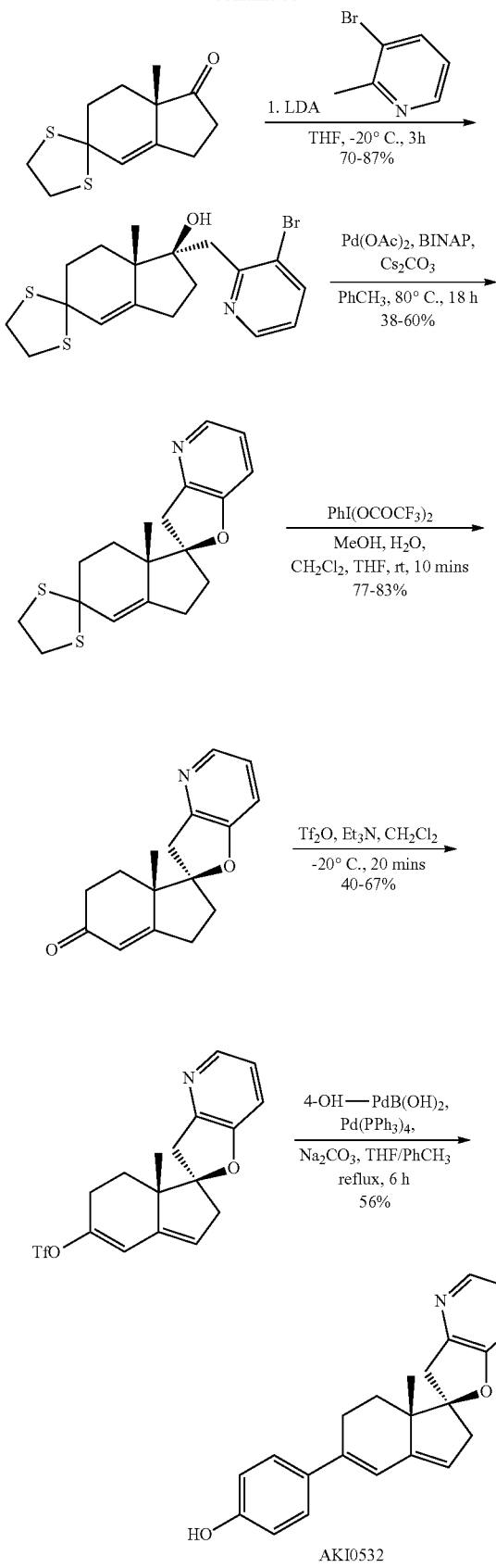
What is claimed is:
1. A compound having the structure:
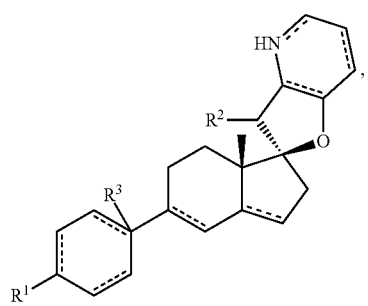
wherein the dashed bonds are present or absent; $R^1$ and $R^2$ are each independently selected from the group of H, —OH, =O, a halo group, a phenyl group, or a $C_{1-6}$ alkyl group; and $R^3$ is H, —OH, or a $C_{1-6}$ alkyl group.
2. The compound of claim 1, wherein said compound is selected from the following:
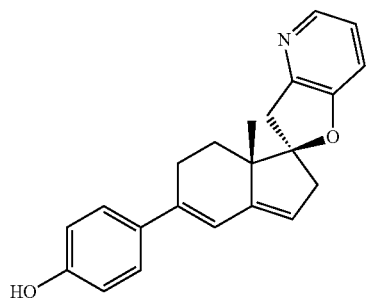
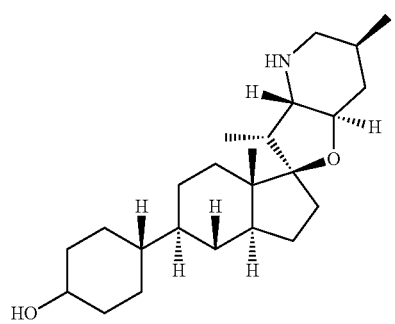
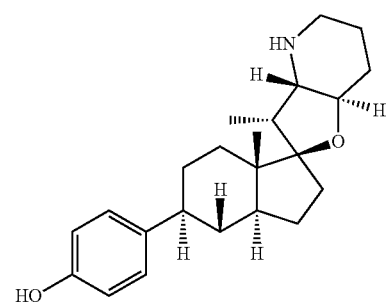

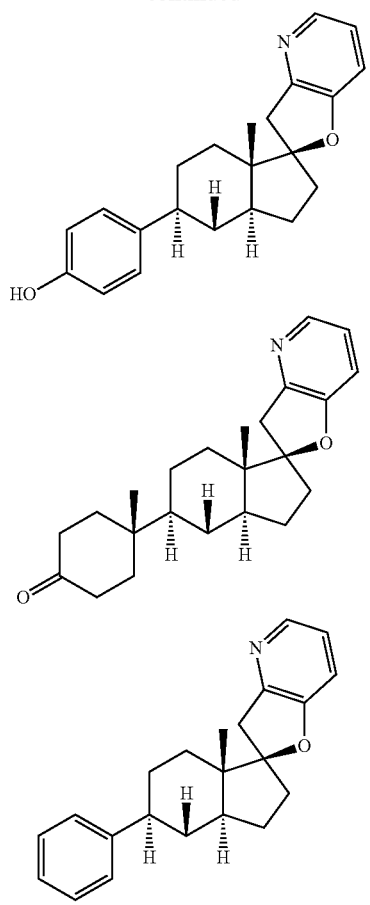

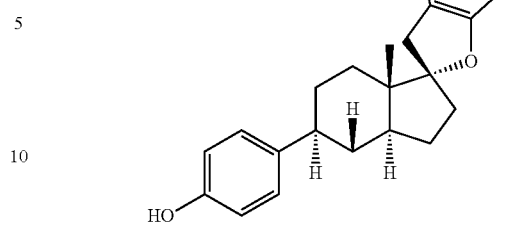

3. A pharmaceutical composition comprising a compound of claim 1 in admixture with a pharmaceutically acceptable carrier.

4. The pharmaceutical composition of claim 3, wherein said composition is formulated for parenteral, transdermal, oral, subcutaneous, intrapulmonary, topical or intranasal administration.

5. A method for inhibiting sonic hedgehog signaling in a cell comprising contacting a cell with a compound of claim 1 thereby inhibiting sonic hedgehog signaling in the cell.

6. The method of claim 5, wherein said method is carried out in vitro.

7. The method of claim 5, wherein the cell is a cancer cell.

8. A method for treating cancer comprising administering to a subject in need of treatment an effective amount of the pharmaceutical composition of claim 3 thereby treating the subject's cancer.

9. The method of claim 8, wherein the cancer is breast cancer, prostate cancer, small cell lung cancer, lung adenocarcinoma, melanoma, pancreatic cancer, basal cell carcinoma, medulloblastoma, or meningioma.

10. The method of claim 9, wherein the cancer has metastasized.

* * * * *